United States Patent [19]

Cuzin et al.

[11] Patent Number: 5,012,498
[45] Date of Patent: Apr. 30, 1991

[54] X-RAY TOMOGRAPHY DEVICE

[75] Inventors: Marc Cuzin, La Tronche; Francis Glasser, Jarrie, both of France

[73] Assignee: Commissariat a l'Energie Atomique, Paris, France

[21] Appl. No.: 300,896

[22] Filed: Jan. 24, 1989

[30] Foreign application Priority Data

Jan. 25, 1988 [FR] France ............... 8800784

[51] Int. Cl.⁵ ................ A61B 6/00; H05G 1/34; F16K 3/00
[52] U.S. Cl. ........................... 378/22; 378/7; 378/19; 378/110; 378/98; 378/4; 378/10; 378/109; 378/21; 250/370.15
[58] Field of Search ............ 378/4, 7, 10, 19, 22, 378/109, 98, 110, 21, 62; 250/370.09, 370.15

[56] References Cited

U.S. PATENT DOCUMENTS

| 4,070,707 | 6/1978 | Barber ............... 378/901 |
| 4,097,741 | 6/1978 | Pfeiler et al. ............ 378/97 |
| 4,255,659 | 3/1981 | Kaurman et al. ......... 378/19 |
| 4,366,382 | 12/1982 | Kotowski ................ 378/57 |
| 4,484,340 | 11/1984 | Yamaguchi et al. ......... 378/16 |
| 4,639,943 | 6/1987 | Heinze et al. ............ 378/97 |
| 4,691,332 | 9/1987 | Burstein et al. .......... 378/7 |

FOREIGN PATENT DOCUMENTS

| 0213213 | 3/1987 | European Pat. Off. . |
| 3244636 | 4/1984 | Fed. Rep. of Germany . |
| 2260252 | 10/1975 | France . |
| 2365328 | 5/1978 | France . |
| 2004436 | 3/1979 | United Kingdom . |
| 8201124 | 4/1982 | World Int. Prop. O. . |

Primary Examiner—Edward P. Westin
Assistant Examiner—Don Wong
Attorney, Agent, or Firm—Oblon, Spivak, McClelland, Maier & Neustadt

[57] ABSTRACT

The invention concerns an X-ray tomograph device.

This device makes it possible to obtain the image (1) of a plane cutting (2) of an object (3). In particular, it comprises an X-ray source (4) which supplies high energy pulses which traverse the object. At least one measurement detector small bar (10) receives the attenuated energy pulses which have traversed the object. A display and processing means connected to the detectors supplies the image of the cutting. These processing means include amplifier-integrator circuits (13) connected to the detectors (10) and to a computer (15) controlling the integration period of the detection pulses suplied by the detectors (10). The computer corrects the value of the amplitude of each detection pulse by talking account of an intermediate integration value so as to take account of the drag of each pulse and the stray current of each detector.

8 Claims, 4 Drawing Sheets

X-RAY TOMOGRAPHY DEVICE

FIELD OF THE INVENTION

The present invention concerns an X-ray tomography device using a pulsed X-ray source.

BACKGROUND OF THE INVENTION

In particular, this invention is applicable to the industrial control of highly absorbant objects with large dimensions and for which it is desired to restore the images of plane cuttings by using a high-energy (for example, greater than several 100 KeV) pulsed X-ray source and means for processing the signals derived from radiation detectors having traversed this object. This invention may also be applied to the control of slightly absorbent objects with small dimensions.

There exists a known type of X-ray tomography device which makes it possible to obtain the image of at least one plane cutting of an object and includes an X-ray source supplying high-energy pulses at a predetermined frequency. This device also includes a primary collimator so that the pulses traverse the object inside a cutting plane and close to the latter. Means are usually provided to support the object and to move it in translation and/or in rotation. This type of device also includes a small bar of measuring detectors receiving the attenuated energy pulses having traversed the object and a secondary collimator placed between the object and the bar of detectors. These detectors respectively supply on outputs electric detection pulses representing the received attenuated energy pulses derived from the object. Finally, this known type of device includes display and processing means connected to the outputs of the detectors in order to supply the image of each cutting of the object. The signals derived from the detectors are generally coded and digitalized so as to enable them to be processed by a computer. In this type of device, the detectors may be constituted by photoelectron multipliers or photodiodes respectively connected to a scintillator.

In this known type of device, the pulsed X-ray source does not present perfect stability and the detection means may present temperature drifts and dark currents and, in the case of a radioactive object, there exists an unwanted detection not taken into account when processing signals. Accordingly, the image of each cutting obtained is not perfect.

When the detection means used are constituted by photoelectron multipliers or photodiodes connected to scintillators, these scintillators age under the effect of radiation thus, the transparency and efficiency of the scintillators become altered after absorbing a certain dose of X-rays. It is then necessary to regenerate the scintillators via a thermal cycle.

Owing to the foregoing, it frequently happens that any tomography device which uses scintillators is not available. Moreover, the volume occupied by a set of scintillators and photodetectors (photoelectron multipliers or photodiodes) limits the possibilities of embodying detection means with a small geometric pitch, which strictly limits the number of measuring points. Finally, the limited dynamics of photoelectron multipliers involves the use of photodiodes for objects with high absorption dynamics, but in this case necessary to take into account two energy conversion efficiencies: the efficiency relating to the conversion of X photons into visible photos and the efficiency relating to the conversion of visible photons into electrical charges. As a result, there is extremely high loss of sensitivity of the devices thus constituted allied with the introduction of significant statistical noise. In general, the scintillation efficiency is extremely low (less than 10%).

Generally speaking, it is therefore preferable to use detection means which make it possible to carry out a direct conversion of the X photons into electrical charges. These detection means usually consist of small bars of detectors containing a semiconductor.

These detectors are used in a known way with low energy continuous radiation sources (normally with X-ray generators fed with a d.c. voltage of about several 10 k volts). These detectors are distributed in the form of a small bar (or a mosaic), each detector being constituted by a semiconductive pellet of small dimensions (about a few mm) inserted between two electrodes, the radiation to be detected arriving under normal incidence at the planes of the detectors and the electrodes.

This geometry of the detectors does not enable said detectors to be used with good efficiency for high energies. In fact, with such a structure, the increase of the thickness of the semiconductive pellet, rendered necessary so as to obtain high energy effectiveness, introduces a large collection distance of the charges created. This introduces two major drawbacks:

the charges can recombine before reaching an electrode, the maximum charges collection time is considerable.

Owing to this, the known tomography devices functioning with high-energy X-ray sources do not use detectors containing a semiconductor.

In known pulsed source tomography devices, the signals supplied respectively by the detectors are pulse signals which present extremely high drag when the flow of X radiations received has extremely high energy. As a result, the pulse signal supplied by a detector after receiving an X-ray pulse having traversed the object may be superimposed on the pulse signal supplied by this detector at the time of receiving the X-ray pulse received previously. Moreover, these detectors, when being irradiated by the pulses originating from the object, present a relatively high temperature drift.

These known tomography devices functioning with high energy X-ray sources process the signals supplied by the detectors without taking account of the drag of the electrical pulse signal supplied by each detector, any temperature drifts provoked by the irradiation of these detectors and the dark current of each detector. These devices no longer take account of the instability of the X-ray pulsed source and any possible radiation emitted by the object itself (radioactive object). As a result, the image of each section of the object is an image of poor quality.

SUMMARY OF THE INVENTION

The object of the invention is to overcome these drawbacks by embodying an X-ray tomography device using a high-energy pulsed source and having at least one small bar of photodetectors, the invention making it possible via suitable means to process the electrical pulse signal derived from each detector whilst taking account of the drag of this signal, the temperature drift of the detectors, the dark current, the instability of the source and any possible radiation emitted by the object. The detectors of the invention are preferably of the semiconductor type and are conceived so as to have sound high energy efficiency and so as to possibly avoid any diffusion of radiations from one detector towards another detector during operation.

According to a first embodiment of the invention, the device includes a small bar of compensation detectors identical to the small bar of measuring detectors and situated close to this small bar of measuring detectors. This small bar of compensation detectors comprised means to render it opaque to the attenuated energy pulses derived from the object. The device also comprises amplifier-integrators circuit each amplifier-integrator comprising a differential amplifier having a first input connected to the corresponding measuring detector, and a second input connected to the corresponding compensation detector, each differential amplifier supplying a detection pulse amplified and compensated according to the temperature drift and dark current of the corresponding measuring detector. The output of the differential amplifier is connected to one input of an integrator having one of said inputs for controlling the integration period and supplying on one output said correction and measurement pulses.

According to one particular embodiment, each amplifier-integrator circuit includes an operational amplifier integrator connection, one input of this operational amplifier receiving the detection pulse originating from the corresponding detector, one input for controlling the integration period of the integrator connection being connected to one corresponding control output of a computer. One output of this operational amplifier is connected to a terminal of a circuit breaker having one opening or closing control input connected to one corresponding control output of the computer, and another terminal of this circuit breaker is connected to the input of the corresponding analog to digital converter.

According to a further embodiment, the device comprises numerical temperature indication means situated close to the small bar of measuring detectors, one output of these indication means supplying a numerical signal indicating the value of the temperature close to the small bar of measuring detectors. This output is connected to one input of the computer so that the latter carries out a correction processing of the numerical values of the actual recorded measurements in order to correct these numerical values according to the temperature drift of the measuring detectors.

According to a further characteristic, the device also comprises a reference detector receiving the pulses from the source and supplying on one input reference detection pulses representative of the energy of the source, an analog to digital converter having one input connected to the output of the reference detector and supplying on one output a numerical value representative of the energy of the source, this output being connected to one input of the computer so that the latter carries out a correction processing of the actual numerical values recorded in order to correct these values according to the energy variations of the source.

According to another characteristic, each detector comprises a semiconductive pellet, each pellet having the form of an elongated parallelepiped defined by its width, height and depth, one face of this parallelepiped defined by the width and height situated opposite the object, two other parallel faces of this parallelepiped defined by the height and depth bearing respectively two electric supply electrodes, one of these electrodes supplying said detection pulses. Advantageously, each electrode is covered with a screening layer opaque to the rays received by the detector and avoiding diffusion in each nearby detector.

According to a further characteristic, an electrically insulating layer is inserted between each electrode and the screening layer.

BRIEF DESCRIPTION OF THE DRAWINGS

The characteristics and advantages of the invention shall be more readily understood from a reading of the following description with reference to the following drawings in which.

DETAILED DESCRIPTION OF THE PREFERRED EMBODIMENTS

Figure 1:
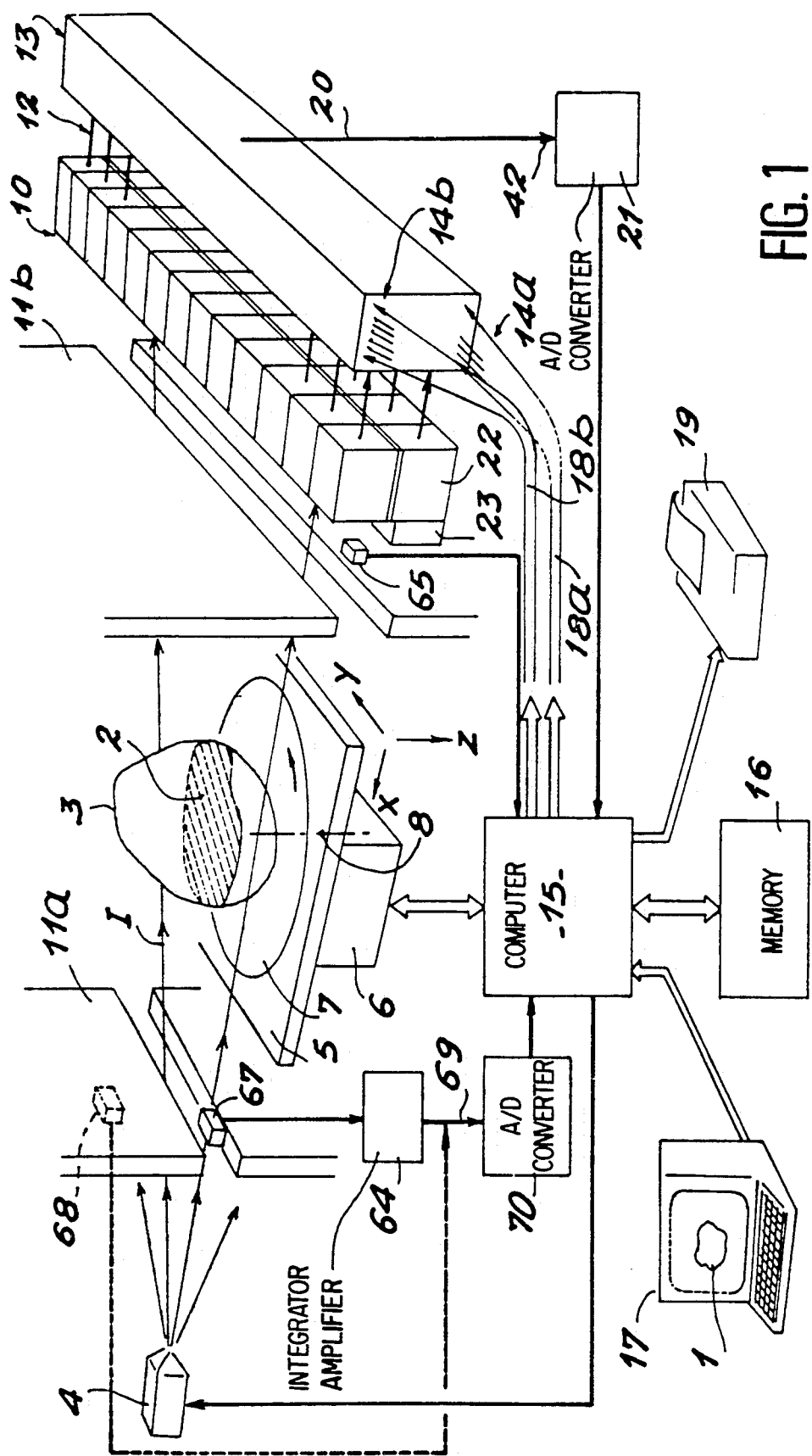
FIG. 1 diagrammatically shows an X-ray tomography device according to the invention.

The X-ray tomography device diagrammatically represented on FIG. 1 makes it possible to obtain the image 1 of at least one plane cutting 2 of an object 3. This device includes an X-ray source 4 supplying high energy pulses at a predetermined frequency. It also includes a primary collimator 11a so that these pulses traverse the object 3 close to the plane defining the cutting 2. This figure clearly diagrammatically shows the pulse beam I. In order to more clearly explain this figure, this beam appears to have an extremely large thickness, but it is clear that its thickness is relatively thin so that the X-ray pulses traverse the object 3 close to the plane, which can be regarded as a cutting plane.

This device also includes means 5, 6 and 7 supporting the object and able, for example, of moving it in translation and/or in rotation. These means may be constituted by a table 5 able to be translation moved parallel to two perpendicular axes Y and Z. It can support a further table 7 able to moved in rotation around an axis 8. The means 6 makes it possible to control the various translation or rotation movements. These means known in the prior Art are not described here in detail. The device also includes a small bar 10 of measuring detectors which receive the attenuated energy pulses having traversed the object, as well as the aperture of a secondary collimator 11b. These detectors respectively supply on outputs 12 electric detection pulses representative of the attenuated energy pulses originating from the object 3. Finally, the device comprises display and processing means which enable the image of the cutting 2 of the object to be obtained from electric pulse signals supplied by the outputs 12 of the detectors of the measuring bar 10.

The display and processing means include a set 13 of integrator-amplifier circuits having inputs respectively connected to the outputs 12 of the measuring detectors. These integrator-amplifier circuits shall be described later in detail. Each integrator-amplifier comprises one input so as to control the integration periods of each pulse signal supplied by the corresponding measuring detector. The set of the integration period control inputs is denoted by the reference 14b on this figure. Moreover, each integrator-amplifier includes one input for controlling reading of the integrated signal, all of these control inputs bearing the reference 14a.

The display and processing means also comprise a computer 15 connected to a memory 16 and display means 17 enabling the cutting 2 of the object 3 to be displayed. This computer has outputs 18a and 18b respectively connected to the control inputs 14a and 14b of the integrator-amplifier circuits 13. The computer may also be connected to a printer 19.

The memory 16 of the computer 15 contains a processing and sequencing program so as to control each integrator-amplifier circuit, as shall be seen later in detail, so that each electric detection pulse supplied by the corresponding detector is integrated as follows: each pulse is integrated onto a first rough measurement period and, after a certain period of time, onto at least a second period. Each integrator-amplifier circuit thus supplies on one output a first rough measurement pulse and a second correction pulse; these pulses respectively have the first and second periods. The amplitude of the first pulse is representative of the energy of the attenuated pulse received by the detector and originating from the object. The amplitude of the second pulse is representative of the drag of the electrical detection pulse supplied by the detector and of the dark current or stray current of the latter and of any possible radiation from the object. One output 20 common, for example, to all the outputs of the integrator circuit 13 is connected to one input 42 of an analog to digital converter 21; one output of this converter is connected to the computer 15; this converter supplies rough measurement and correction numerical values respectively representative of the amplitudes of the first and second correction and measuring pulses for each of the detectors. The computer processes these numerical values so as to supply the actual numerical values of the measurements of the energies of the attenuated pulses received by the detectors. These actual numerical values are recorded in the memory 16 of the computer 15. The actual numerical values thus recorded for all the detectors are used by the computer so as to control display of the image 1 of the cutting 2 on the screen of the display means 17.

In practice, so as to increase the speed for processing the pulses supplied by the detectors and in order to simplify the connections, the integrator-amplifier circuits are advantageously regrouped into several units or sub-units: each sub-unit is connected to one input of an analog to digital converter whose output is connected to the computer. These sub-units respectively combine, for example, ten integrator-amplifier circuits.

By successively scrutinizing them by means of the reading control inputs 14a and the common output 20, each converter receives between two integration phases the signals of the integrator-amplifier circuits connected to it.

Figure 2:
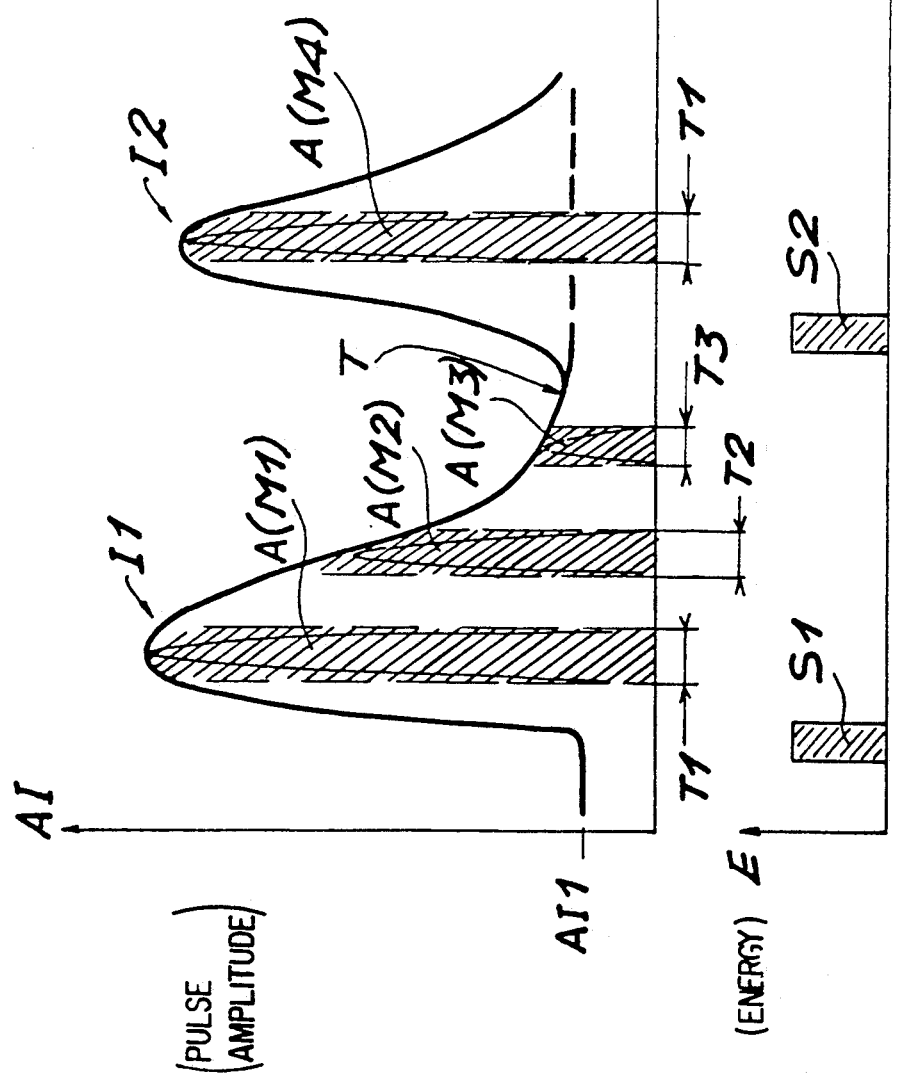
FIGS. 2A and 2B are diagrams representing the pulse signals obtained at the output of a detector of the device of the invention, FIG. 3 diagrammatically shows a first mode for embodiment of the small bar of compensation and measuring detectors used in the device of the invention, FIG. 4 diagrammatically shows a further embodiment of an integrator-amplifier circuit used in the device of the invention, FIG. 5 diagrammatically shows a further embodiment of an integrator-amplifier used in the device of the invention, FIG. 6 diagrammatically shows a first embodiment of a small bar of measuring detectors used in the device of the invention, FIG. 7 diagrammatically shows a further embodiment of a small bar of measuring detectors used in the device of the invention.

FIGS. 2A and 2B are diagrams which make it possible to better understand the sequencing and processing of the detection signals supplied by the detectors. FIG. 2A shows, according to the time t, the amplitude variations AI of two successive detection pulses I1, I2 supplied by the output of one of the detectors 10.

FIG. 2B represents the energy E according to the time t of the pulsed radiations emitted by the source 4. These energy variations are represented here as an example by two successive pulses S1, S2. The detection pulses I1, I2 at the output of one of the detectors are synchronous with the pulses S1, S2. In the absence of receiving an attenuated energy radiation pulse, each detector delivers a stray current or dark current of amplitude A1I. As the pulses received by each detector present high energy, this results in the detection pulse I1 having a drag T which disturbs the detection pulse I2 whose start amplitude should be A1I.

As indicated earlier, the sequencing and processing for each detection pulse, such as I1, consists of integrating this pulse on at least one second correction period T2 within the time interval which separates this detection pulse I1 from the next detection pulse I2. It is also possible to integrate the pulse I1 on a third correction period T3 which, as shall be seen later in detail, makes it possible to carry out a more precise correction of measurement of the energy received by the detector in question. The integration of the pulse I1 on the period measuring period T1 supplies a rough measurement pulse M1 whose amplitude is representative of the energy of the radiation pulse received by the detector if account is not taken of disturbance due to the drag of the previous pulse, the dark current or the stray current of the detector and to any possible radiation from the object. Similarly, integration of the pulse I1 on the correction period T2 supplies a second correction pulse M2 whose amplitude is representative of the drag of the pulse I1, the stray or dark current of the detector or of any possible radiation from the object. The third pulse M3 resulting from integration onto a third o correction period M3 also presents an amplitude A(M3) representative of the drag, dark current or stray current and any possible radiation from the object. The measurement and correction pulses M1, M2, M3 are applied to the analog to digital converter 21 by the output of the integrator-amplifier circuit. Sequencing of the integration periods is controlled by the computer 15. The actual values corresponding to the amplitudes A(M1), A(M2), A(M3) of the pulses M1, M2, M3 are recorded in the memory 16 of the computer. The computer then corrects the actual value representative of the amplitude M1 of the rough measurement pulse of the energy received by the detector by subtracting from this rough measurement actual value an actual value linked to the amplitude of the correction pulse M2 or by subtracting an actual value linked to the amplitudes of the correction pulses M2 and M3. As the amplitudes of the pulses M2 and M3 are representative of the drag of the signal I1 and the stray current of the corresponding detector and any possible radiation from the object, the computer then records in its memory an actual numerical value, which more precisely is representative of the value of the energy received by the detector.

It is supposed in this example that the rough measurement correction is effected by means of the actual values corresponding to the pulses M2, M3 concerning the actual value of the amplitude of the pulse M1. It would be Possible to carry out this correction concerning the rough measurement actual value of the amplitude A(M4) of the pulse M4 representing integration on the period T1 of the next pulse T2 supplied by the detector. Thus, it is possible to take account of the drag present in a detection pulse, either concerning this pulse or concerning the next detection pulse.

According to a further embodiment, the device of the invention comprises another bar of compensation detectors 22 identical to the bar of measuring detectors; this bar of compensation detectors is situated close to the bar of measuring detectors. This bars of detectors shall be described subsequently in detail; the bar of compensation detectors comprises means, such as a screening, rending it opaque to the attenuated energy pulses I originating from the object 3.

In this embodiment, the effects of the stray current no longer occur as these are compensated by the compensation bar and via a differential measurement of the currents of the detectors, as shall be seen subsequently in detail.

Figure 3:
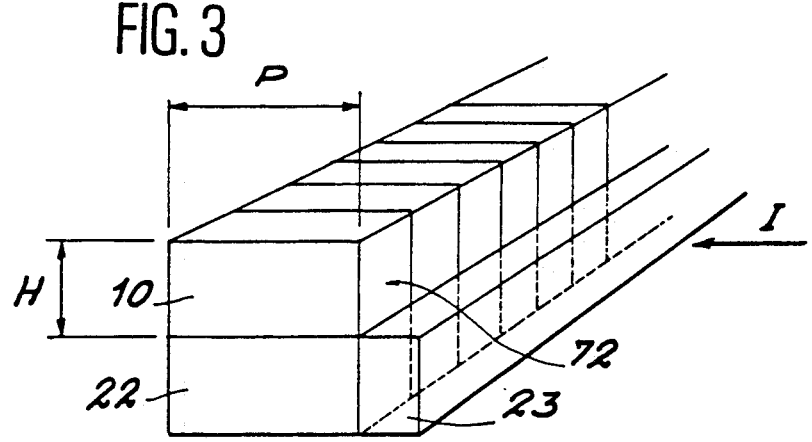

The bar of measuring detectors 10, the bar of compensation detectors 22 and the screening 23 are revealed more clearly on FIG. 3. This figure shows that the screening 23 prevents the radiation pulses I from reaching the compensation detectors 22, even though these pulses reach the measuring detectors 10. The role of the bar of compensation detectors 22 shall be subsequently described in detail.

Figure 4:
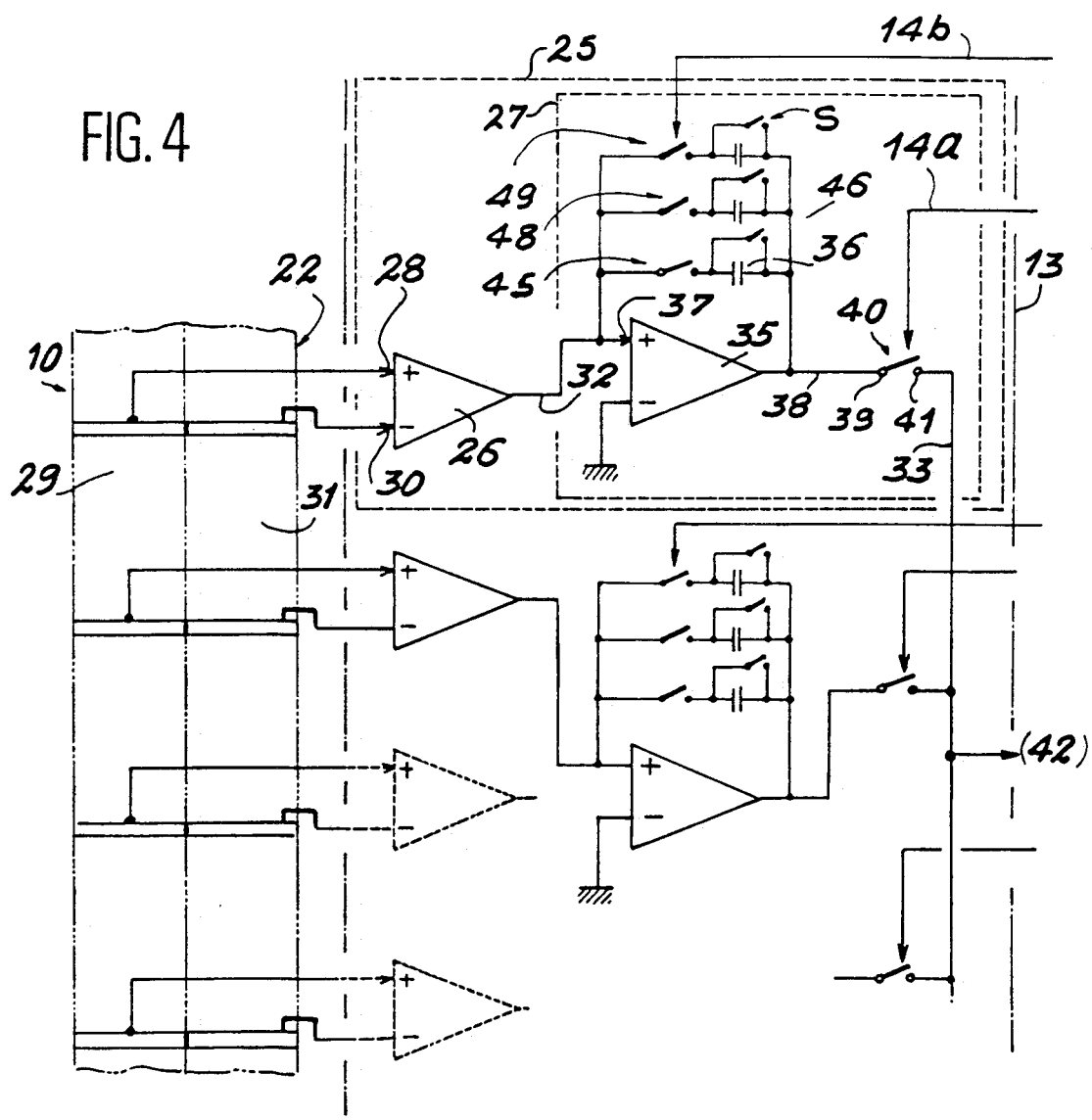

FIG. 4 diagrammatically shows a first embodiment of the integrator-amplifier circuits 13 used in the device of the invention. In this embodiment, it is supposed that the device includes a bar of measuring detectors receiving the radiation pulses originating from the object and a bar of compensation detectors provided with a screening (not shown) rendering it insensitive to the radiation pulses originating from the object.

In this embodiment, each integrator-amplifier circuit, such as the circuit 25 of the unit 13, comprises a differential amplifier 26 and an integrator 27. The differential amplifier 26 has one first input 28 connected to one electrode of the corresponding measuring detector 29 of the measuring bar 10, and one second input 30 connected to one electrode of the corresponding compensation detector 31 of the compensation bar 22. Each differential amplifier, such as the amplifier 26, supplies on one output 32 detection pulses amplified and compensated according to the temperature drift and dark current of the measuring o detector. These pulses are synchronous with the pulses received originating from the object. As the measuring and compensation detectors are identical and at the same temperature, they undergo the same drifts. These drifts are thus compensated by the differential amplifier 26. As the compensation detector 31 has a screening opaque to the radiation pulses received by the measuring detector, the signal supplied by this compensation detector is also representative of the dark current of the measuring detector 29.

The output 32 of the differential amplifier 26 is connected to one input of the integrator 27. This integrator comprises said control inputs 14a and 14b connected to one corresponding control output 18a and 18b of the computer 15. This integrator supplies on one output 33 of said correction and measuring pulses obtained by integration on at least the first and second periods mentioned earlier. The other integrator-amplifier circuits connected to the other detectors of the compensation and measuring bars are identical to the integrator-amplifier circuit just described.

Each integrator circuit 27 includes an operational amplifier connection. This connection comprises an operational amplifier 35 and at least one integration capacitor 36. This operational amplifier receives on its input 37 the amplified detection pulse originating from the corresponding differential amplifier 26. Another input of the amplifier 35 is connected to a reference potential. One output 38 of the operational amplifier integrator connection is connected to a terminal 39 of an opening and closing circuit breaker 40. This control is precisely effected by a signal supplied by the control output 18a of the computer 15. This signal is successively applied to the control input 14a corresponding to the circuit breaker 40 for each amplifier-integrator circuit of the unit or sub-units of these circuits between two integrations. A further terminal 41 of the circuit breaker 40 constitutes the output 33 of the integrator-amplifier 27. This output is an output common to the integrator-amplifier circuits of the unit or sub-unit of these circuits; it is connected to the input 42 of the corresponding analog to digital converter 21.

Preferably and according to the amplitudes of the detection pulses to be integrated, each integrator-amplifier circuit includes several integration capacitors 36, 46, 47 respectively connected between the output and input of the operational amplifier 35 by means of circuit breakers 45, 48, 49 controlled by a signal supplied by the control output 18b of the computer 15 and applied to the control input 14b. The capacitors 36, 46, 47 have capacities of different values. The choice of one of the capacitors via one of the circuit breakers 45, 48, 49 makes it possible to predeterminedly fix the amount of maximum charges which each integrator can take into account. In fact, according to the amplitude of the detection pulses for which the integration operations are to be carried out and according to the conversion scale of the analog to digital converter, it may be useful to predeterminedly select the amount of maximum charges for each integrator. The choice of capacitors is also linked to the integration periods (T1, T2, T3) previously defined; the integration periods are linked to the closing period of the corresponding circuit breakers. The choice of capacitors and integration periods is carried out during a stage for prior calibration of the device.

After each integration and, more precisely, after the corresponding converter has received the output signal from the integrator-amplifier circuit, it is proper to reset the corresponding integrator by discharging one of the integration capacitors 36, 46 or 47 used, for example, with the aid of a field effect transistor shown on the figure by means of a circuit breaker S connected in parallel with the capacitor 47 in question. A circuit breaker is connected in parallel with each integration capacitor. Of course, it is possible to have a single circuit breaker connected in parallel to all these capacitors. Resetting controlled by the transistor is carried out automatically in an analog way by means of a delay circuit linked to the closing control of the circuit breaker 40, namely directly by the computer from the processing program.

Figure 5:
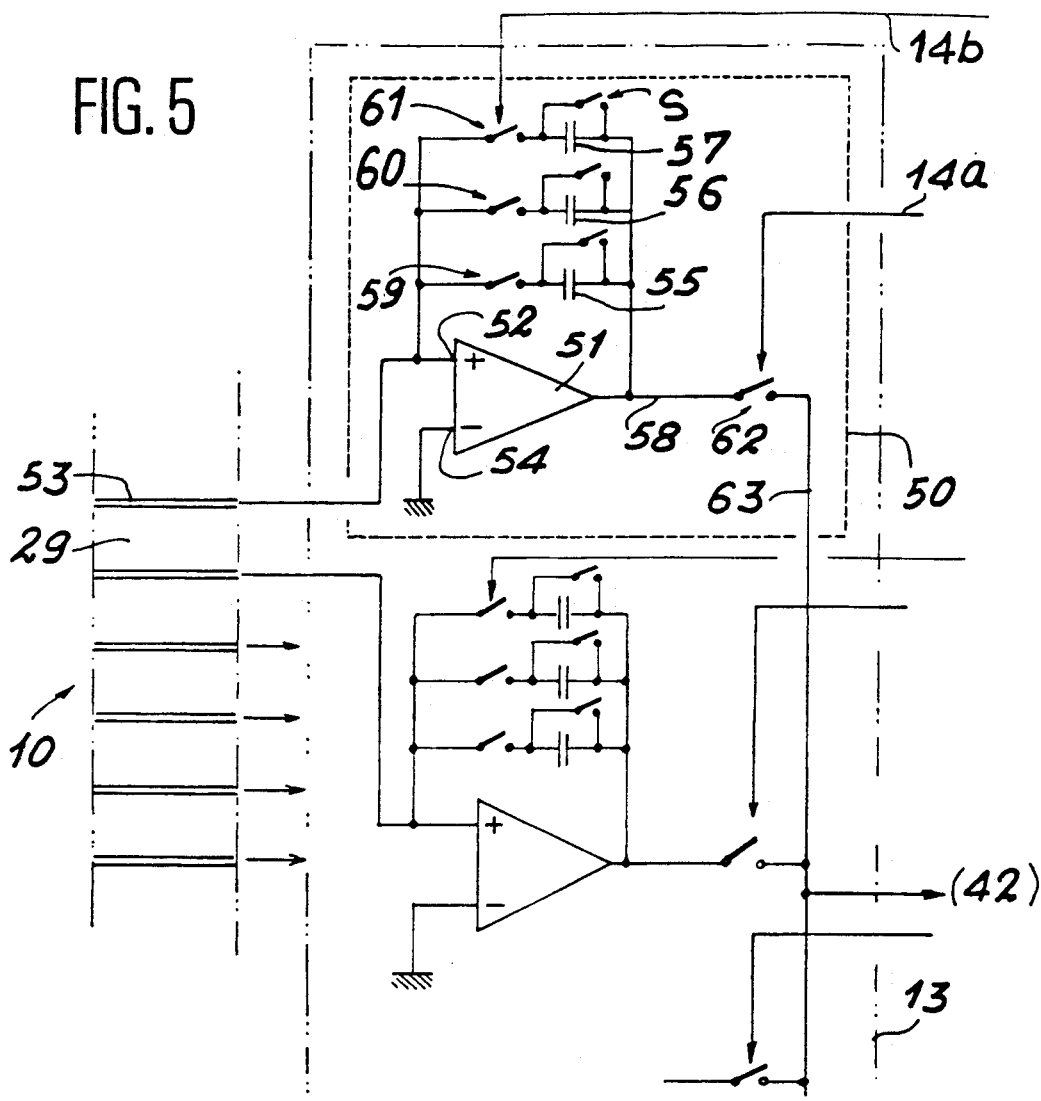

FIG. 5 diagrammatically represents a further embodiment of the integrator-amplifier circuit used in the device of the invention. Only one of these integrator-amplifier circuits 50 belonging to the set of integrator-amplifier circuits 13 shall be described here in detail. In this embodiment, it is supposed that the device does not comprise a bar of compensation detectors, but only a bar 10 of measuring detectors. In this case, the integrator-amplifier circuit 50 includes an operational amplifier integrator connection 51 similar to the connection 27 of FIG. 4.

This operational amplifier comprises one input 52 connected to an output electrode 53 of a corresponding detector 29. This electrode supplies detection pulses. The other input 54 of the operational amplifier 51 is connected to a reference potential. As in the preceding connection, integration capacitors 55, 56, 57 connected in parallel between the input 52 of the operational amplifier 51 and the output 58 of this amplifier may be respectively selected by circuit breakers 59, 60, 61 controlled by signals originating from the output 18b of the computer and applied to an input 14b. The predetermined choice of one of these capacitors makes it possible to fix the maximum quantity of the charges of the integrator circuit. This integrator circuit also comprises, as in the preceding connection, resetting means represented by circuit breakers respectively connected to the integration capacitors and a circuit breaker 62 whose opening or closing is controlled by signals originating from the output 18a of the computer and which are applied to an input 14a. This input is one of the control inputs 14a of the unit or sub-unit of the integrator-amplifier circuits. As previously, the circuit breakers 59, 60, 61 make it possible to fix the various integration periods described earlier. The other integrator-amplifier circuits are identical to those just described. The output 63 of the integrator-amplifier 50 forms an output common to the unit 20 or to a sub-unit of the outputs of the integrator-amplifier circuits. It is connected to the input 42 of the corresponding analog to digital converter 21.

In this embodiment, each integrator-amplifier circuit supplies correction and measurement pulses, such as those described above. These pulses mentioned here do not make it possible to take into account the temperature drifts of the bar 10 of measuring detectors. It is therefore useful in this embodiment to connect the bar 10 of measuring detectors (the bar of compensation detectors being absent) to numerical temperature indication means 65 (FIG. 1). These temperature indication means are situated close to the bar 10 of measuring detectors. These numerical means 65 supply on one output a digital signal representative of the value of the temperature in the proximity of the bar 10 of measuring detectors. This output is connected to one input of the computer 15. In this case, the memory of the computer comprises calibration tables making it possible to determine for each temperature the current drifts of the measuring detectors. The computer then carries out in a known way a correction calculation of the actual numerical values of measurements already recorded in the memory and corresponding to the measurement of the energy of the pulses originating from the object. The temperature measurement makes it possible to improve precision of the actual recorded values.

Regardless of the embodiment selected, the device moreover includes a reference detector 67 (FIG. 1) making it possible to measure the energy of the pulses derived directly from the source 4. This reference detector may be situated either directly in the pulse beam I, in other words in the aperture of the collimator 11a, or situated as shown as 68 between the source 4 and the collimator 11a outside the direct beam of the pulses I emitted towards the object 3. This reference detector supplies on one output reference energy detection pulses representative of the energy of the source. The detector 67 may be constituted in a known way and shall not be described here in detail. This detector may also be constituted as one of the measuring detectors of the bar 10 and may possibly be associated with one of the integrator-amplifier circuits 64 whose structure is comparable to that of the integrator-amplifier circuits described earlier. The analog to digital converter 70 receives a pulse representative of the energy of the source 4. The reference detector 67 is particularly important as, because the source is pulsed and possesses high energy, the pulses it supplies may present energy fluctuations. The computer records the numerical values of the energy of the source pulses during functioning and corrects the actual numerical values recorded according to the energy variations of the source. These energy measurements of the source pulses enable the precision of the actual recorded values to be improved.

Figure 6:
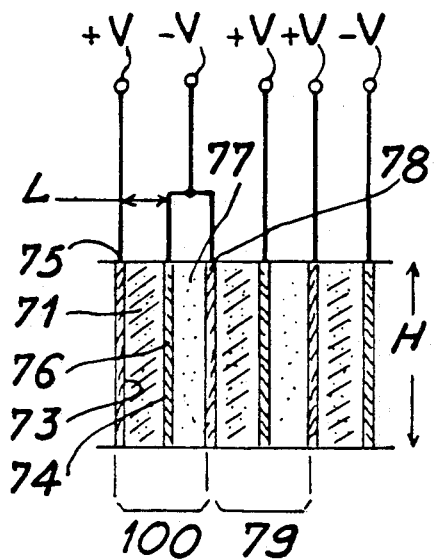

FIG. 6 shows a first embodiment of a bar of detectors used in the device of the invention. These detectors are of the high resistivity (more than $10^5$ $\Omega$.cm) semiconductive type. They may use, for example, one of the following semiconductors: CdTe(Cl), HgI$_2$, AsGa, InP(Fe), Bi$_{12}$GeO$_{20}$, Bi$_{12}$SiO$_{20}$.

Each detector, such as the detector 100 on this figure, comprises a semiconductive pellet 71 having the shape of an elongated parallelepiped defined by its width L, height H and its depth P (the latter being greater than or equal to 1 cm) (see FIG. 3). FIG. 6 solely shows the height H and width L. One face of the parallelepiped 71, which forms the semiconductive Pellet, is situated opposite the object so as to receive the radiation pulses originating from this object (face 72 on FIG. 3). Two other parallel faces 73, 74 of the semiconductive pellet and defined by the height H and depth P respectively carry two electric supply ($+V$, $-V$) electrodes 75 and 76. One of the electrodes, such as the electrode 75, supplies the detection pulses mentioned above.

Each electrode is advantageously covered with a screening layer 77 opaque to the rays diffused by the detector. This screening layer makes it possible to reduce crosstalk between neighbouring detectors, i.e. to limit the diffusion of photons between neighbouring detectors. In this embodiment, the electrodes 76 and 78 of two adjacent detectors 100 and 79 are connected to the common supply terminal $-V$. In the case of this embodiment example, screening must be electrically insulating.

Figure 7:
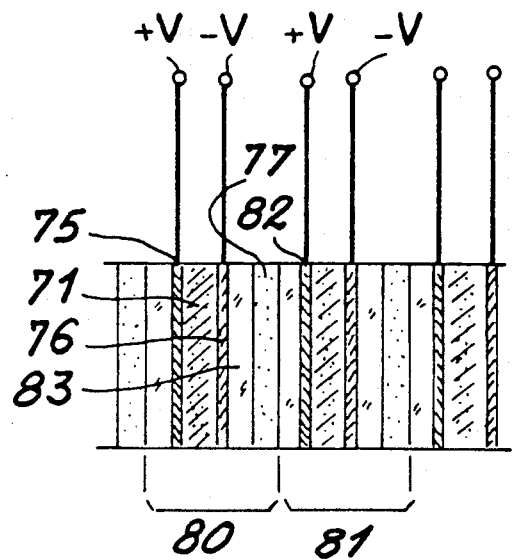

FIG. 7 diagrammatically shows a further embodiment of the detectors of the device of the invention. Two of these detectors are shown as 80 and 81 on this figure. In this other embodiment, each detector also comprises a semiconductive pellet 71 with a parallelepiped shape and having on two parallel faces the electrodes 75 and 76. In this embodiment, the adjacent electrodes 76 and 82 of the two adjacent detectors 80 and 81 are not brought to the same potential, but to different potentials $-V$ and $+V$. Moreover, screening is, for example, metallic and thus each detector must comprise, apart from the screening layer 77, an electrically insulating layer 83 situated between each electrode, such as 76, and the screening layer, such as 77.

The representation given for the measuring detectors 10 and compensation detectors 22 corresponds to the independent detectors 10 and 22, but of course they may be advantageously embodied from a given semiconductive pellet having on two parallel faces two pairs of electrodes corresponding to the electrodes of the detectors 10 and 22.

The device just described makes it possible to attain the above-mentioned objectives: it allows a satisfactory image of a cutting of an object to be obtained by means of a correction of the amplitude measurements of the detection pulses; this correction takes account of the drag of each pulse signal supplied by each detector, the dark current, any possible radiation from the object, any temperature drifts and any energy fluctuations of the pulse source.

What is claimed is:

1. An X-ray tomography device for obtaining the image of at least one plane cutting, of an object, comprising:

an X-ray source for supplying high-energy pulses at a predetermined frequency;

a primary collimator for directing the high-energy pulses so that the high-energy pulses traverse the object close to a cutting plane;

at least one bar of photoelectric measuring detectors for receiving the high-energy pulses which have been attenuated by the object and have passed through a secondary collimator, these photoelectric detectors respectively supplying electric detection pulses representative of the attenuated energy pulses originating from the object;

display and processing means connected to the photoelectric measuring detectors so as to supply an image of said at least one plane cutting;

means for translating and moving the object;

the display and processing means include a set of integrator-amplifier circuits connected to the photoelectric measuring detectors, each integrator-amplifier circuit having means for controlling an integration period;

a computer connected to a memory and to said display means and having control outputs respectively connected to the integrator-amplifier circuits, the memory of the computer containing a sequencing and processing program so as to control each integrator-amplifier circuit so that each electric detection pulse supplied by a corresponding photoelectric detector is integrated during a first rough measurement period and so as to integrate this electric detection pulse on at least one second correction detection pulse from the next electric detection pulse;

each integrator-amplifier circuit supplying an analog to digital converter a first rough measurement pulse and a second correction pulse having duration corresponding to the first rough measurement period and the at least one second correction period, the amplitude of the first rough measurement pulse representative of the energy of the attenuated energy pulses originating from the object which are received by the photoelectric measuring detectors, the amplitude of the second pulse being representative of the drag of the electric detection pulses supplied by the photoelectric measuring detectors and any possible radiation from the object, the analog to digital converter having one output connected to the computer so as to supply numerical values respectively representative of the amplitudes of the first rough measurement pulse and of the second correction pulse;

the computer processing these numerical values for each electric detection pulse so as to supply one actual numerical value measuring the energy of the attenuated energy pulse received by the photoelectric measuring detectors, this actual numerical value being recorded in the memory, the actual numerical values thus recorded for all the photoelectric measuring detectors being used by the computer so as to control display of the image of said at least one plane cutting by the display means and wherein the amplitude of the second correction pulse is also representative of the stray current of the photoelectric measuring detectors.

2. Device according to claim 1, further comprising a bar of compensation detectors identical to the bar of photoelectric measuring detectors and situated close to the bar of compensation detectors comprising means to render it opaque to the attenuated energy pulses derived from the object, each integrator-amplifier circuit comprising a differential amplifier having one input connected to the corresponding photoelectric measuring detector, and a second input connected to the corresponding compensation detector, each differential amplifier supplying on one detection pulse amplified and compensated according to the temperature drift and the dark current of the corresponding photoelectric measuring detector, the output of this differential amplifier being connected to an integrator, one control input having an integration period and supplying on one output and supplying on one output of said first rough measurement pulse and of said second correction pulse.

3. Device according to claim 1, wherein each integrator-amplifier circuit includes an operational amplifier integrator connection, one input of this operational amplifier receiving the electric detection pulse originating from the corresponding compensationj detector, one input for controlling the integration period of the integrator connection being connected to one corresponding output of the computer, one output of this operational amplifier being connected to a terminal of a circuit breaker having one closing or opening control input connected to one corresponding control output of the computer, another terminal of this circuit breaker being connected to the input of the corresponding analog to digital converter.

4. Amplifier according to claim 2, wherein each integrator amplifier includes an operational amplifier integrator connection, one input of this operational amplifier receiving the amplified detection pulse derived from the corresponding differential amplifier, one input for controlling the integration period of the integrator connection being connected to a corresponding control output of the computer, one output of the operational amplifier connection being connected to a terminal of a circuit breaker having one opening or closing control input connected to one corresponding output of the computer, another terminal of this circuit breaker being connected to the input of the corresponding analog to digital converter.

5. Device according to claim 3, further comprising numerical temperature indication means situated close to the bar of photoelectric detectors, one output of these indication means supplying one digital signal indicating the value of the temperature drift of the bar of photoelectric measuring detectors, this output being connected to one input of the computer so that the latter can carry out a correction processing of the actual measurement values recorded so as to correct these numerical values according to the temperature drift of the bar of photoelectric measuring detectors.

6. A device according to claims 4 or 5, further comprising a reference detector receiving the pulses of the X-ray source and supplying on one output reference detection pulses representative of the energy of the X-ray source, one analog to digital converter having one input connected to the output of the reference detector and supplying on one output a numerical value representative of the energy of the source, this output being connected to one input of the computer so that the latter can carry out a correction processing of the actual recorded numerical values in order to correct these values according to the energy variations of the source.

7. Device according to claim 6, wherein each of photoelectric detector comprises a semiconductive pellet, each pellet having the shape of an elongated parallelepiped defined by its width, height and its depth, one face of this parallelepiped defined by the width and height being situated opposite the object, two other parallel faces of this parallelepiped defined by the height and depth respectively carrying two electric supply electrodes, one of these electric supply electrodes supplying said electric detection pulses, each electric supply covered with a screening layer opaque to the rays received by the photoelectric measuring detectors and avoiding diffusion in each neighbouring detector.

8. Device according to claim 7, wherein an electrically insulating layer is inserted between each electric supply electrode and the screening layer.

* * * * *